(12) United States Patent
Lauf et al.

(10) Patent No.: US 10,265,109 B2
(45) Date of Patent: Apr. 23, 2019

(54) SPINE PLATE IMPLANT WITH CAM LOCK BONE SCREW RETENTION

(71) Applicant: Life Spine, Inc., Huntley, IL (US)

(72) Inventors: Garrett D. Lauf, Elgin, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 159 days.

(21) Appl. No.: 15/422,447

(22) Filed: Feb. 1, 2017

(65) Prior Publication Data

US 2017/0215930 A1    Aug. 3, 2017

Related U.S. Application Data

(60) Provisional application No. 62/290,027, filed on Feb. 2, 2016.

(51) Int. Cl.
| | | |
|---|---|---|
| *A61B 17/80* | (2006.01) | |
| *A61B 17/70* | (2006.01) | |
| *A61B 17/86* | (2006.01) | |

(52) U.S. Cl.
CPC ...... *A61B 17/8047* (2013.01); *A61B 17/7059* (2013.01); *A61B 17/8033* (2013.01); *A61B 17/8042* (2013.01); *A61B 17/8057* (2013.01); *A61B 17/8605* (2013.01)

(58) Field of Classification Search
CPC ............ A61B 17/8033; A61B 17/8038; A61B 17/8042
See application file for complete search history.

(56) References Cited

U.S. PATENT DOCUMENTS

| | | | | |
|---|---|---|---|---|
| 7,288,094 | B2 * | 10/2007 | Lindemann | A61B 17/7059 606/86 A |
| 7,875,062 | B2 * | 1/2011 | Lindemann | A61B 17/8042 606/280 |
| 9,119,677 | B2 * | 9/2015 | Jacene | A61B 17/1728 |
| 2009/0163960 | A1 | 6/2009 | Binder et al. | |
| 2012/0277803 | A1 | 11/2012 | Remesh et al. | |
| 2013/0060337 | A1 | 3/2013 | Petersheim et al. | |
| 2015/0094772 | A1 | 4/2015 | Black et al. | |

OTHER PUBLICATIONS

Search Report for International Application No. PCT/US2017/016177, dated Apr. 20, 2017, 13 pages.

* cited by examiner

*Primary Examiner* — Nicholas W Woodall
(74) *Attorney, Agent, or Firm* — Foley & Lardner LLP

(57) ABSTRACT

A spine plate implant utilizes cam lock setscrews to retain bone screws in the plate once implanted. A cam lock setscrew is received in a setscrew pocket adjacent a configured bone screw bore of the plate and is configured to allow a bone screw to be received in the plate when in an unlocked rotational position, and to retain the received bone screw when in a locked rotational position. The bone screw includes a tang that allows engagement with external teeth of the cam lock setscrew when the cam lock setscrew is rotated into the locked position. Once the cam lock setscrew is in the locked position, the bone screw is inhibited from backing out of the bone screw bore. When the cam lock setscrew is in the unlocked position, a flat of the cam lock setscrew is adjacent the bone screw tang so the bone screw may be removed.

14 Claims, 6 Drawing Sheets

SPINE PLATE IMPLANT WITH CAM LOCK BONE SCREW RETENTION

CROSS-REFERENCE TO RELATED APPLICATIONS

This U.S. non-provisional patent application claims the benefit of and/or priority under 35 U.S.C. § 119(e) to U.S. provisional patent application Ser. No. 62/290,027 filed Feb. 2, 2016 titled "Spine Plate Implant With Cam Lock Bone Screw Retention," the entire contents of which is specifically incorporated herein by reference.

FIELD OF THE INVENTION

The present invention relates to orthopedic implants such as plates and screws for the spine and, more particularly to spine plate implants having screw retention features.

BACKGROUND OF THE INVENTION

People content with spine issues as a result of age, disease, trauma, and congenital and acquired complications and conditions. While some of these issues can be alleviated without surgery, other issues respond better to surgery. In some cases, surgery may include installing an orthopedic implant.

One type of orthopedic implant for the spine is a plate or plate construct along with bone screws for attaching the plate/plate construct to vertebrae of the spine. Various spine plates have been developed over the years for general, particular and specific use. However, with most, if not all of the spine plates there is an issue known as back out where one or more of the bone screws unscrews (backs out) from the plate. This compromises the integrity of the orthopedic implant and its ability to perform its intended function.

While numerous spine plate implants have been designed over the years to combat bone screw back out, they are deficient in many respects. It is therefore an object of the present invention to provide an orthopedic plate implant that overcomes the deficiencies of the prior art.

SUMMARY OF THE INVENTION

The present invention is a spine plate implant that utilizes cam lock setscrews to retain bone screws that are received in the spine plate. Each cam lock setscrew is situated adjacent a configured bone screw bore of the spine plate and is configured to allow a bone screw to pass by the cam lock setscrew and be received in the spine plate when in one rotational position (an unlocked, open, or neutral position), and to retain the bone screw received in the spine plate when in another rotational position (a locked, closed, or engaged position).

The present spine plate implant includes a spine plate, a plurality of cam lock setscrews, and a plurality of bone screws. The spine plate has a plurality of bone screw bores each one configured to receive a bone screw and a pocket adjacent each bone screw bore, each pocket configured to receive a cam lock setscrew. The bone screw is configured to allow engagement with the cam lock setscrew when the cam lock setscrew is rotated into a locked position. Once the cam lock setscrew is in the locked position, the bone screw is inhibited from backing out of the bone screw bore. When the cam lock setscrew is in an unlocked position, the bone screw may be backed out of the bone screw bore.

Each cam lock setscrew has external threads that engage with threading in the setscrew pocket to provide rotational stability, engagement, and positioning of the cam lock setscrew with the setscrew pocket. External teeth are provided about a portion of the outer diameter of each cam lock setscrew for engagement with the bone screw when the cam lock setscrew is rotated into the locked position. An external flat is provided about a portion of the external teeth of the cam lock setscrew that allows the bone screw to be received in the spine plate when the cam lock setscrew is rotated into the unlocked position.

The bone screw includes one or more tangs, flanges, or the like about an upper area of the bone screw that provide engagement with the external teeth of the cam lock setscrew when the cam lock setscrew is in the locked position. When the cam lock setscrew is in the unlocked position, the external flat is adjacent a tang, flange, or the like of the bone screw permitting the bone screw to pass by the cam lock setscrew for removal of the bone screw from the bone screw bore.

Further aspects of the present invention will become apparent from consideration of the drawings and the following description of a form of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate a form of the present invention, wherein.

DETAILED DESCRIPTION OF THE INVENTION

Figure 1:
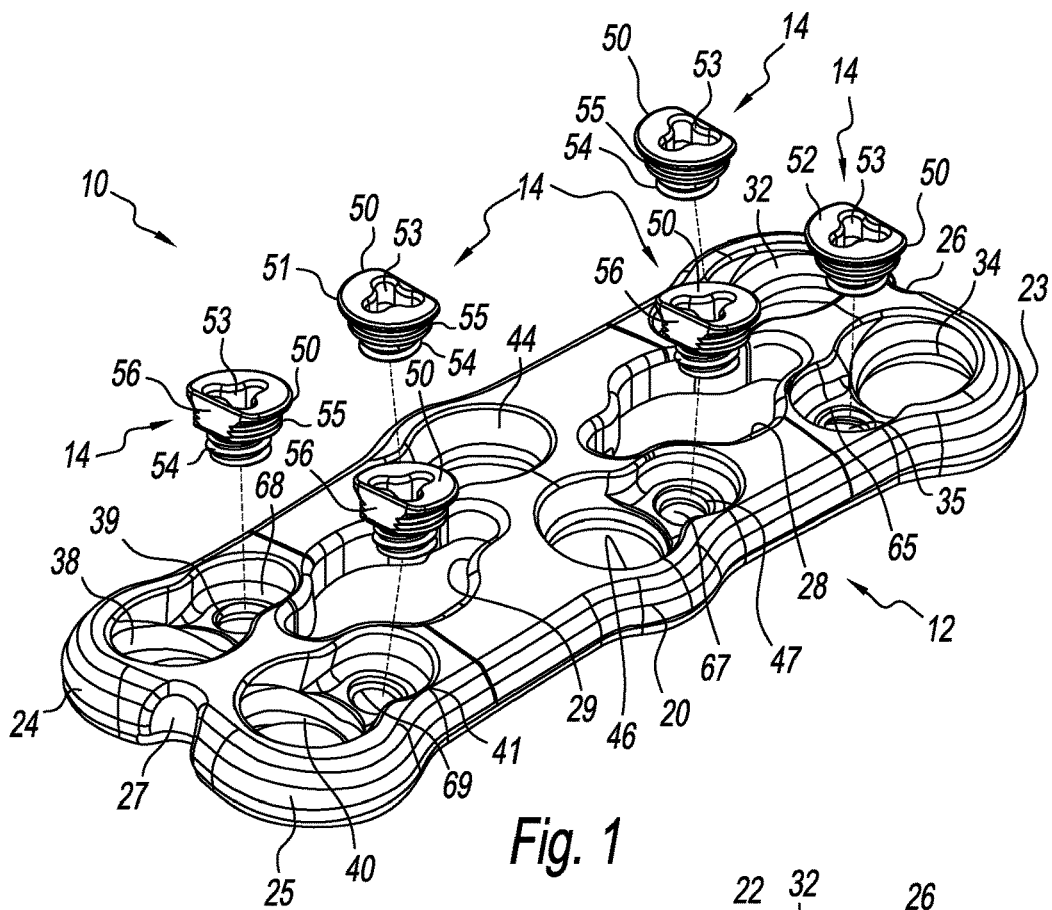
FIG. 1 is an exploded isometric view of an exemplary cervical plate implant fashioned in accordance with the present principles.

Referring to the figures, there is depicted an exemplary form of a spine plate implant, generally designated 10. The spine plate implant 10 is made from a biocompatible material such as, but not limited to, titanium, stainless steel, an alloy of titanium or stainless steel, or other. The spine plate implant 10 is characterized by a spine plate 12, a plurality of cam lock setscrews 14, and a plurality of bone screws 60. While the spine plate implant 10 is particularly for the cervical portion of the spine, it can be used for other portions of the spine.

Figure 3:
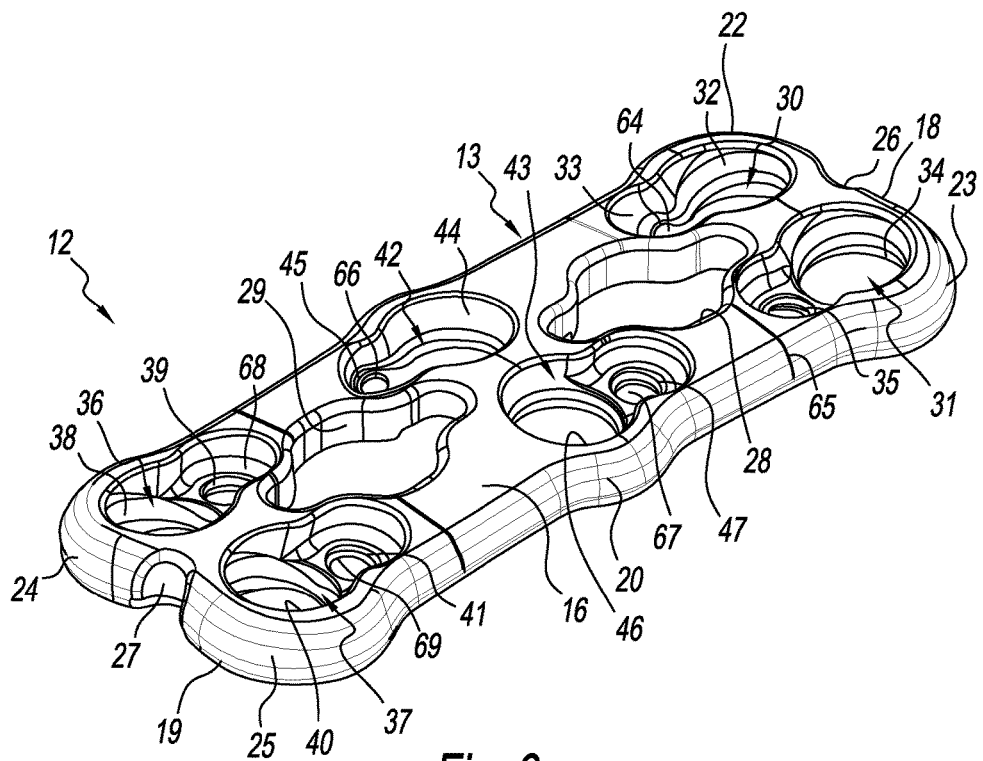
FIG. 3 is an isometric view of the plate of the cervical plate implant of FIG. 1.
Figure 4:
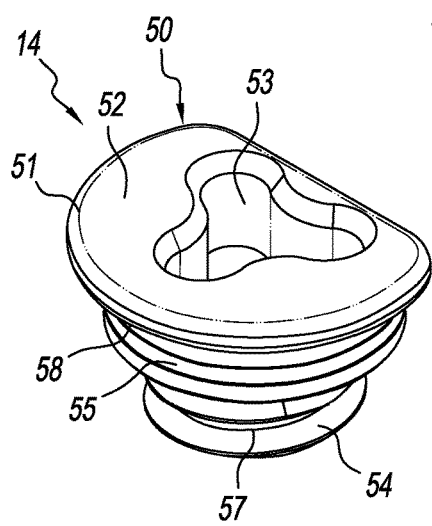
FIG. 4 is an enlarged isometric view of one side of the cam lock setscrew of the cervical plate implant of FIG. 1.
Figure 5:
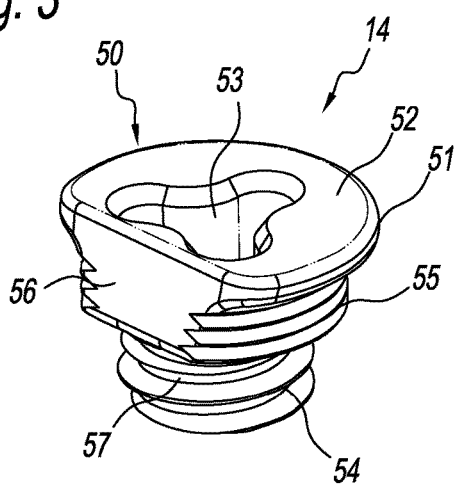
FIG. 5 is an enlarged isometric view of another side of the cam lock setscrew of FIG. 4.
Figure 6:
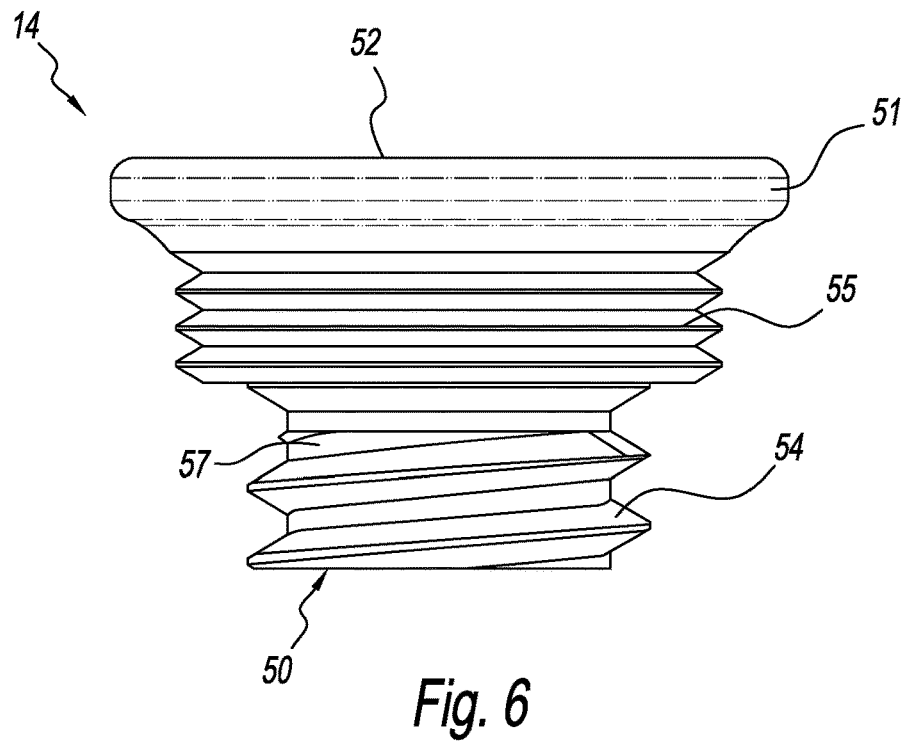
FIG. 6 is an enlarged side view of the cam lock setscrew of FIG. 4.
Figure 10:
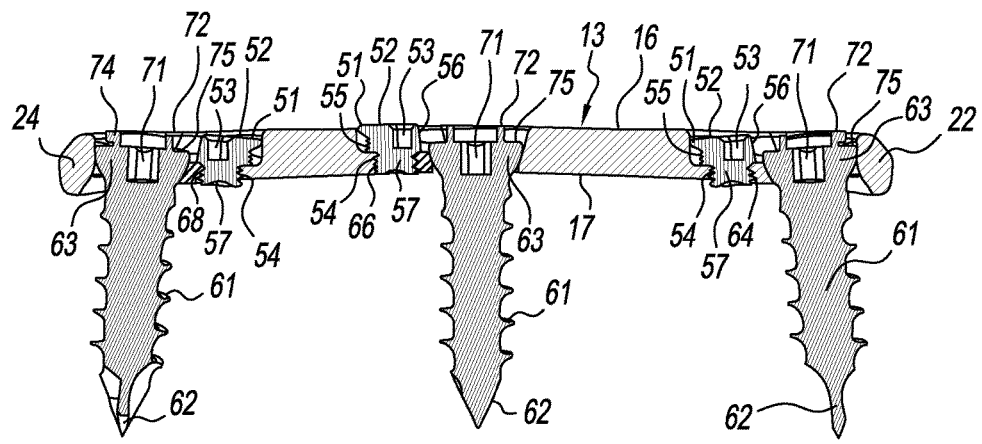
FIG. 10 is a sectional view of the cervical plate implant as shown in FIG. 9 with bone screws received in the plate and the cam lock setscrews in the unlocked position.

FIG. 3 depicts the spine plate 12. The spine plate 12 is characterized by an elongated body 13 having a generally planar upper surface 16 and a generally planar lower surface 17. The body 13 defines a first end 18, a second end 19, and a middle 20, with the nomenclature first and second being arbitrary. The first end 18 has a first boss 22 at one side thereof, and a second boss 23 at another side thereof opposite to the first boss 22, the nomenclature first and second again being arbitrary. A notch 26 is provided in the periphery of the first end 18 between the first boss 22 and the second boss 23. A first configured cavity 30 is provided at the first boss 22 while a second configured cavity 31 is provided at the second boss 23, the nomenclature first and second again being arbitrary. The first configured cavity 30 includes a bore 32 that is structured to receive a bone screw 60, and a pocket 33 adjacent the bore 32 that is structured to receive a cam lock setscrew 14. Particularly, the bone screw bore 32 is structured to angle a received bone screw 60 outwardly from the bottom of the body 13 as best seen in FIG. 10, while the cam lock setscrew pocket 33 includes screw threads 64 about its inner lower periphery. The second configured cavity 31 includes a bore 34 that is structured to receive a bone screw 60, and a pocket 35 adjacent the bore 34 that is structured to receive a cam lock setscrew 14. Particularly, the bone screw bore 34 is structured to angle a received bone screw 60 outwardly from the bottom of the body 13 in like manner as received bone screw 60 from the bone screw bore 32, while the cam lock setscrew pocket 35 includes screw threads 65 about its inner lower periphery.

The second end 19 has a first boss 24 at one side thereof, and a second boss 25 at another side thereof opposite to the first boss 24, the nomenclature first and second again being arbitrary. A notch 27 is provided in the periphery of the second end 19 between the first boss 24 and the second boss 25. A first configured cavity 36 is provided at the first boss 24 while a second configured cavity 37 is provided at the second boss 25, the nomenclature first and second again being arbitrary. The first configured cavity 36 includes a bore 38 that is structured to receive a bone screw 60, and a pocket 39 adjacent the bore 38 that is structured to receive a cam lock setscrew 14. Particularly, the bone screw bore 38 is structured to angle a received bone screw 60 outwardly from the bottom of the body 13 as best seen in FIG. 10, while the cam lock setscrew pocket 39 includes screw threads 68 about its inner lower periphery. The second configured cavity 37 includes a bore 40 that is structured to receive a bone screw 60, and a pocket 41 adjacent the bore 40 that is structured to receive a cam lock setscrew 14. Particularly, the bone screw bore 41 is structured to angle a received bone screw 60 outwardly from the bottom of the body 13 in like manner as the bone screw 60 from the bone screw bore 34 of the first end 18, while the cam lock setscrew pocket 41 includes screw threads 69 about its inner lower periphery.

The middle 20 of the body 13 has a first configured cavity 42 at a first side of the middle 20 while a second configured cavity 43 is provided at a second side of the middle 20, the nomenclature first and second again being arbitrary. The first configured cavity 42 includes a bore 44 that is structured to receive a bone screw 60, and a pocket 45 adjacent the bore 44 that is structured to receive a cam lock setscrew 14. Particularly, the bone screw bore 44 is structured to project a bone screw 60 downwardly from the bottom of the body 13 as best seen in FIG. 10, while the cam lock setscrew pocket 45 includes screw threads 66 about its inner lower periphery. The second configured cavity 43 includes a bore 46 that is structured to receive a bone screw 60, and a pocket 47 adjacent the bore 46 that is structured to receive a cam lock setscrew 14. Particularly, the bone screw bore 46 is structured to project a received bone screw 60 downwardly from the bottom of the body 13 in like manner as the received bone screw 60 from the bone screw bore 44 of the first side of the middle 20, while the cam lock setscrew pocket 47 includes screw threads 67 about its inner lower periphery.

The body 13 also includes a first window or opening 28 situated between the middle 20 of the body 13 and the first end 18, and a second window or opening 29 situated between the middle 20 and the second end 19, the nomenclature first and second, again being arbitrary. The first and second windows 28, 29 have generally the same shape, but may be different if desired. As well, the particular shape of the first and second windows 28, 29 may be changed as desired.

Figure 11:
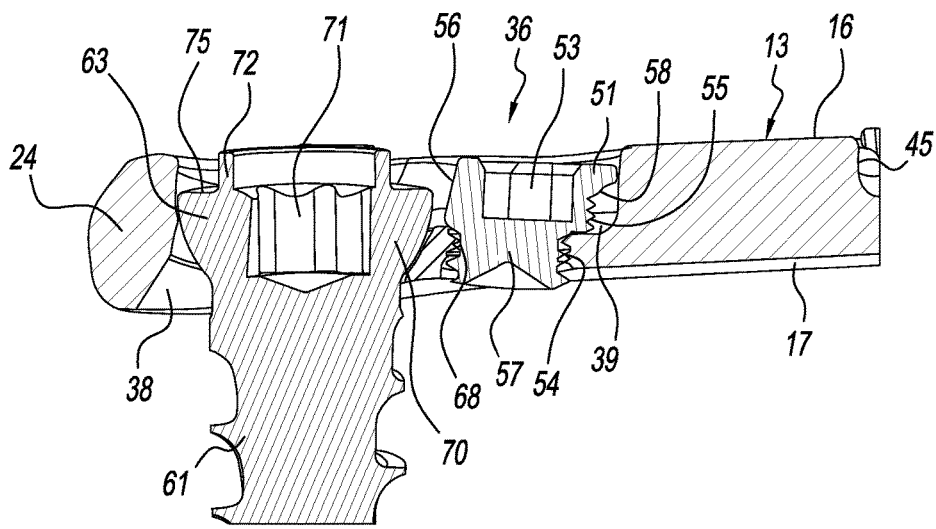
FIG. 11 is an enlarged sectional view of an end screw cavity of the plate of the cervical plate implant with a bone screw and cam lock setscrew received therein, the cam lock setscrew in an unlocked position.
Figure 12:
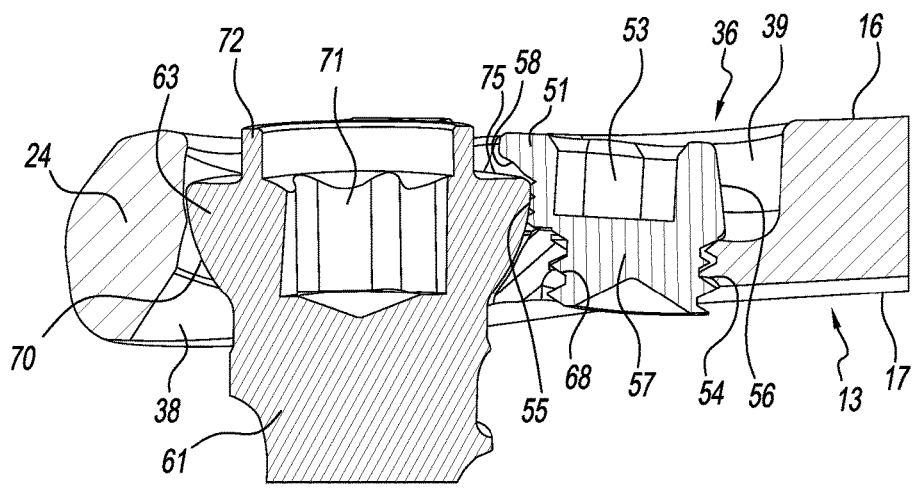
FIG. 12 is an enlarged sectional view of the end screw cavity of the plate of the cervical plate implant with a bone screw and cam lock setscrew received therein of FIG. 11, the cam lock setscrew in a locked position.

The bone screw 60 of the present spine plate implant 10 is depicted in various figures. The bone screw 60 is characterized by an externally threaded shank 61 having a distal tip 62 and a proximal head 63, the shank threading configured for reception in spinal bone. As best seen in FIGS. 11 and 12, the underside 70 of the head 63 is rounded to allow reception of the bone screw head 63 in the bone screw opening of the spine plate 12. The bone screw 60 has a socket 71 in the top of the head 63 for receipt of a driving tool (not shown). While the socket is shown as hexagonally configured, the socket may have other configurations. An annular wall 72 extends from the upper surface 75 of the head 63 and about the socket 71. A first tang, flange or the like 73 extends from one side of the annular wall 72, while a second tang, flange or the like 74 extends from another side of the annular wall 72, preferably, but not necessarily, opposite to the first tang 73, the nomenclature first and second being arbitrary. While two tangs are shown, the bone screw may have more tangs or in the alternative, have a single annular tang extending from the annular wall.

Figure 7:
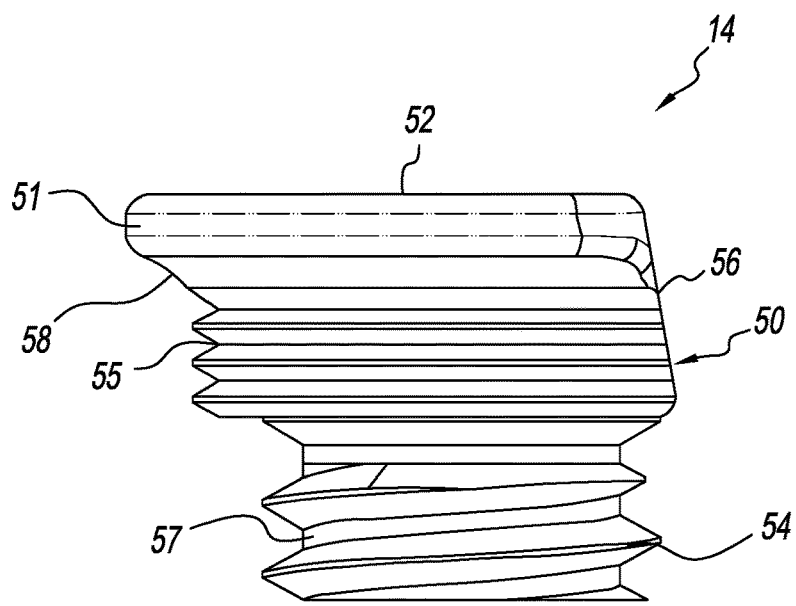
FIG. 7 is an enlarged side view of the cam lock setscrew of FIG. 4.
Figure 8:
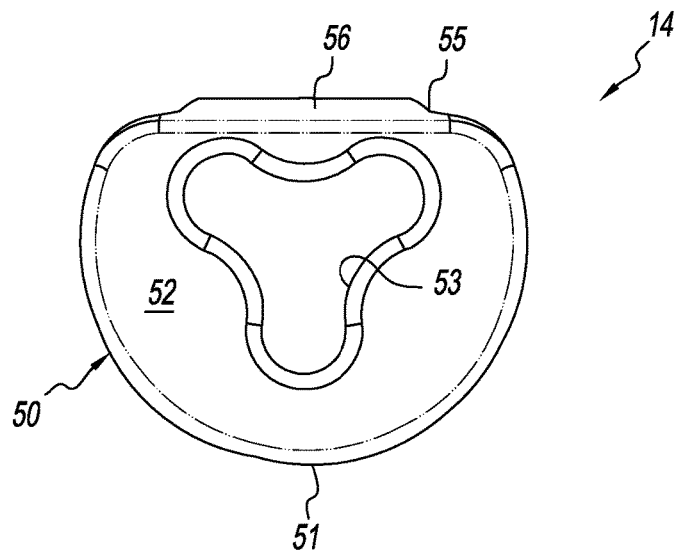
FIG. 8 is an enlarged top view of the cam lock setscrew of FIG. 4.
Figure 9:
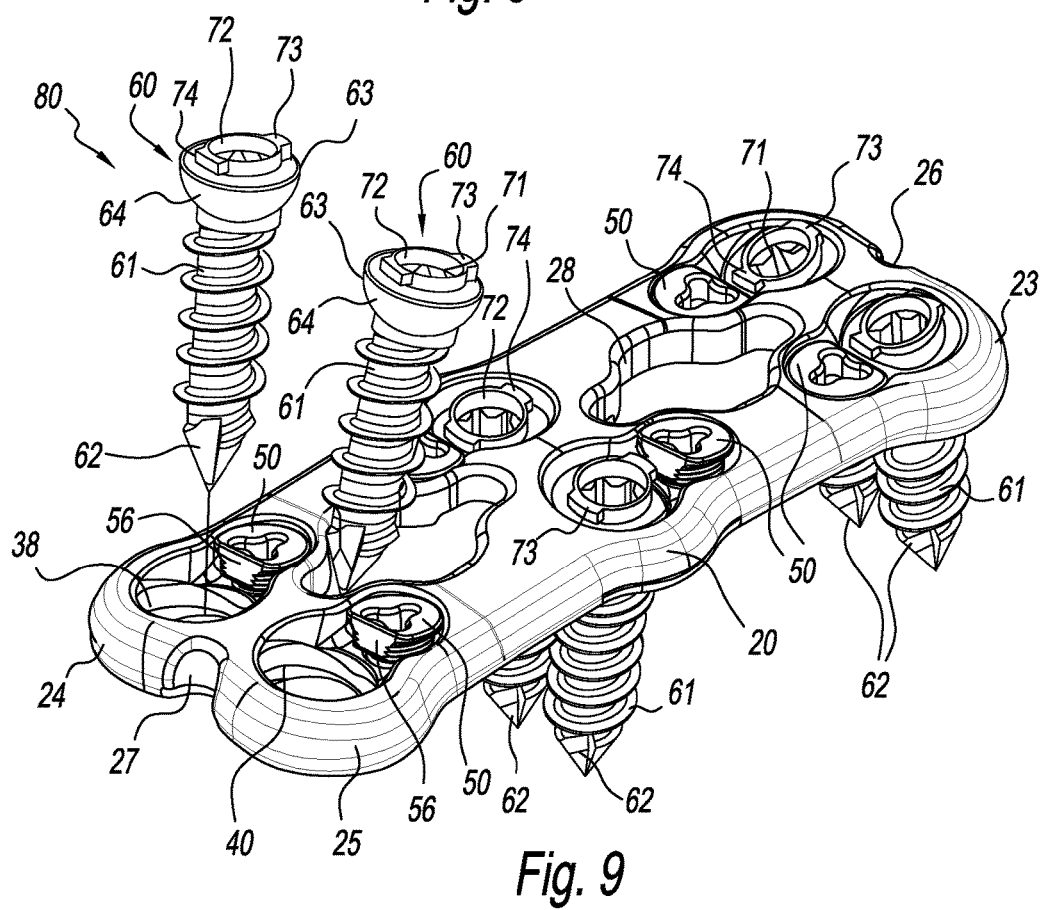
FIG. 9 is an isometric view of the cervical plate implant of FIG. 1 with the cam lock setscrews situated in the plate along with several bone screws received in the plate with two bone screws thereof awaiting insertion into the plate, the cam lock setscrews all in an unlocked or neutral position.

Referring now to FIGS. 4-8, the cam lock setscrew 14 is shown. The cam lock setscrew 14 is characterized by a generally cylindrical body 50 having a neck 57 and a head 51. The head 51 has a generally planar upper surface 52 with a socket 53 situated therein. The socket 53 is configured as a geometric shape for receiving a like shaped tool or instrument (not shown) in order to install the cam lock setscrew 14 into a setscrew pocket of the spine plate, and to lock the cam lock setscrew 14 once a bone screw 60 has been installed onto the spine plate. The neck 57 of the cam lock setscrew 14 has external threading 54 that is sized for reception by the threading of a setscrew pocket of the spine plate. In accordance with an aspect of the present invention, the body 50 has external teeth or the like 55 about a portion of its periphery underneath the head 51 and above the neck threading 54. As best seen in FIGS. 7, 11 and 12, the head 51 has a lip 58 situated generally above the teeth 55. The teeth 55 and lip 58 of the cam lock setscrew 14 cooperate to retain a bone screw 60 as/when the cam lock setscrew 14 is rotated in/into the locked position. The head 51 further has a flat or the like 56 that is generally situated opposite the lip 58. The flat 56 extends through the teeth 55 and allows a bone screw 60 to pass by the cam lock setscrew 14 situated in a setscrew pocket of the spine plate 12 as the bone screw 60 is being received in the adjacent bone screw bore (i.e. the cam lock setscrew is in the open, unlocked, or neutral position). Rotation of the flat 56 away from the bone screw 60 rotates the teeth 55 into the underside 70 of the head 63 of the bone screw 60 engaging the teeth 55 with the bone screw head 63 and positioning the lip 58 over the bone screw head 63 and preferably over a tang 73, 74 (see, e.g. FIGS. 12,13) to lock the teeth 55 of the cam lock setscrew 14 into the bone screw 60 holding the bone screw 60 in place (the closed, locked, or engaged position).

Figure 2:
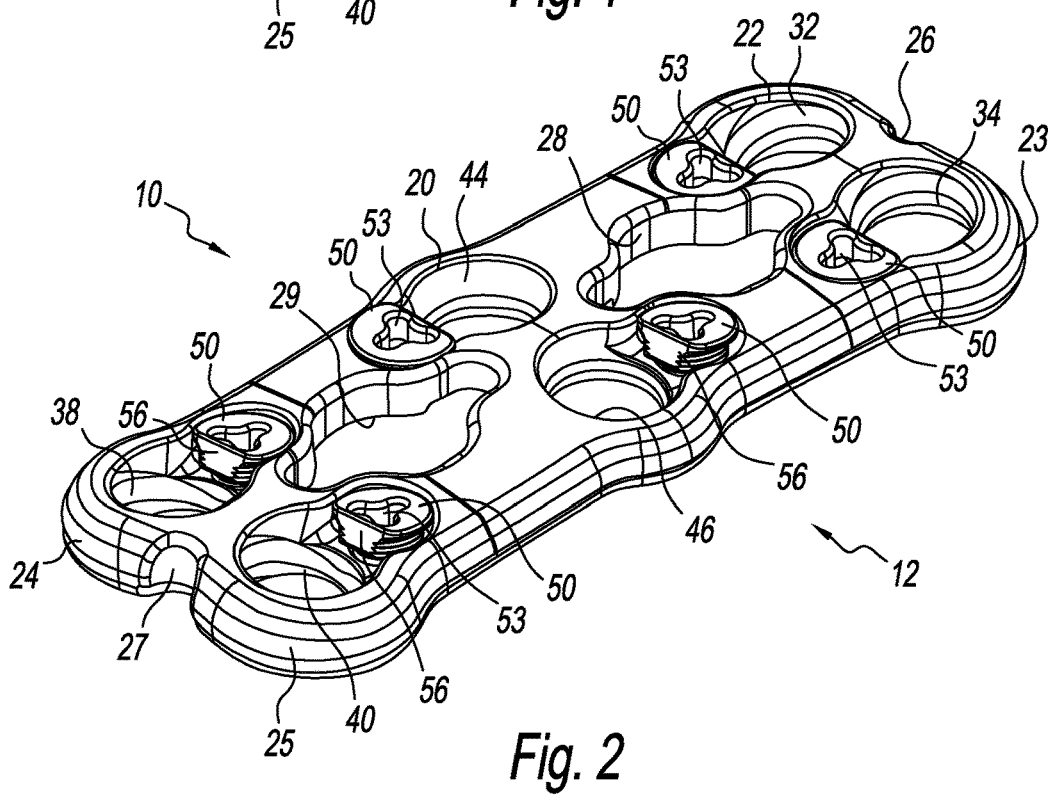
FIG. 2 is an isometric view of the cervical plate implant of FIG. 1, assembled, with the cam lock setscrews thereof situated in the plate thereof.
Figure 13:
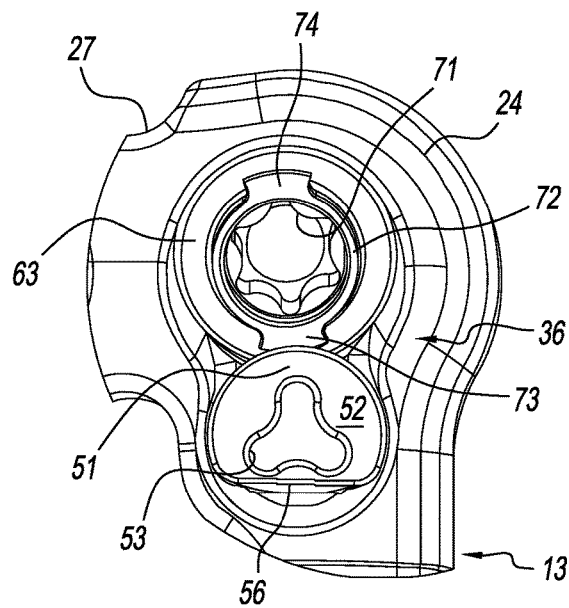
FIG. 13 is an enlarged top view of the end screw cavity of the plate of the cervical plate implant with a bone screw and cam lock setscrew received therein of FIG. 11, the cam lock setscrew and bone screw in a locked position.

FIG. 1 shows a plurality of cam lock setscrews 14 being inserted in respective cam lock setscrew pockets of the spine plate 12. The cam lock setscrews 14 are threadedly received in the respective cam lock setscrew pockets. FIG. 2 shows the plurality of cam lock setscrews 14 received in their respective cam lock setscrew pockets, with each cam lock setscrew 14 in the unlocked position ready to accept a bone screw. FIGS. 10-11 show bone screws 60 received in the spine plate 12 with the associated cam lock setscrews in the unlocked position. FIGS. 12-13 show a bone screw 60 received and retained in the spine plate 12 with the associated cam lock setscrew in the locked position.

The cam lock setscrews 14 are initially in the neutral or open position to allow a bone screw 60 to pass through and into the associated bone screw opening. Once the bone screw is fully seated into the bone screw opening the cam lock setscrew is turned clockwise until it abuts against the head of the bone screw, thus locking the bone screw in place and preventing the bone screw from backing out.

It should be appreciated that dimensions of the components, structures, and/or features of the present spine plate implant may be altered as desired within the scope of the present disclosure.

What is claimed is:

1. A spine implant comprising:
   a plate;
   a plurality of bone screws; and
   a plurality of setscrews;
   the plate having a plurality of bores each one configured to receive one of the plurality of bone screws, and a threaded pocket adjacent each one of the plurality of bores for receiving one of the plurality of setscrews;
   each one of the plurality of bone screws having a head and a threaded shaft extending from a lower side of the head, and a first tang extending from an upper side of the head;
   each one of the plurality of setscrews having a body with external threading on a lower portion of the body that is configured for threaded reception in one of the plurality of threaded pockets, a lip on and extending partially around an upper portion of the body, and a flat on one side of the body and located opposite the lip;
   each setscrew having a first rotational position when installed in a threaded pocket of the plate wherein the lip of the setscrew engage the first tang of a bone screw situated in an adjacent bone screw bore such that backout of the bone screw is prevented, and a second rotational position when installed in a threaded pocket of the plate wherein the flat of the setscrew is adjacent the bore such that a bone screw can be inserted into or removed from the bore without restriction.

2. The spine implant of claim 1, wherein each one of the plurality of setscrews has a configured socket in an upper surface of the body.

3. The spine implant of claim 2, wherein each one of the plurality of setscrews has an overhang situated in the body opposite the flat.

4. The spine implant of claim 1, wherein the plate further has an opening in a middle portion thereof.

5. The spine implant of claim 1, wherein each one of the bone screws has a second tang extending from an upper side of the head opposite the first tang.

6. The spine implant of claim 1, wherein each one of the plurality of bores has a spherical inner perimeter.

7. A spine plate implant comprising:
   a spine plate;
   a plurality of bone screws; and
   a plurality of setscrews;
   the spine plate having a plurality of spherical bores each one configured to receive one of the plurality of bone screws, and a threaded pocket situated radially adjacent each one of the plurality of bores;
   each one of the plurality of bone screws having a head with an upper side and a spherical underside, a threaded shaft extending from the spherical underside of the head, and a first tang radially extending from the upper side of the head;
   each one of the plurality of setscrews having a body defining a cap with an upper surface and a lower surface, external threading on a lower portion of the body that is configured for threaded reception in one of the plurality of threaded pockets, external teeth axially adjacent the lower surface of the cap, and a flat on one side of the body and extending through a portion of the cap and the external teeth;
   each setscrew having a first rotational position when installed in a threaded pocket of the plate wherein the external teeth of the setscrew engage the head of a bone screw situated in an adjacent bone screw bore such that backout of the bone screw is prevented, and a second rotational position when installed in a threaded pocket of the plate wherein the flat of the setscrew is adjacent the bore such that a bone screw can be inserted into or removed from the bore without restriction.

8. The spine plate implant of claim 7, wherein each one of the plurality of setscrews has a configured socket in the upper surface of the cap.

9. The spine implant of claim 8, wherein each one of the plurality of setscrews has an overhang extending from the cap opposite the flat.

10. The spine implant of claim 7, wherein the spine plate further has an opening in a middle portion thereof.

11. The spine implant of claim 7, wherein each one of the bone screws has a second tang extending from the upper side of the head opposite the first tang.

12. The spine implant of claim 7, wherein each one of the plurality of setscrews further comprises a lip located opposite the flat and between the external teeth and the upper surface of the cap, wherein in the first rotational position the lip of the setscrew engages the first tang of the bone screw situated in the adjacent bone screw bore.

13. The spine implant of claim 1, wherein each one of the plurality of setscrews further comprises external teeth on an upper portion of the body between the external threads and the lip, wherein in the first rotational position the external teeth of the setscrew engage the head of the bone screw situated in the adjacent bone screw bore.

14. A spine implant comprising:
a plate;
a plurality of bone screws; and
a plurality of setscrews;
the plate having a plurality of bores each one configured to receive one of the plurality of bone screws, and a threaded pocket adjacent each one of the plurality of bores for receiving one of the plurality of setscrews;
each one of the plurality of bone screws having a head and a threaded shaft extending from a lower side of the head, and a first tang extending from an upper side of the head;
each of the plurality of setscrews comprising:
a body with external threading on a lower portion of the body that is configured for threaded reception in one of the plurality of threaded pockets;
external teeth on an upper portion of the body;
a lip on and extending partially around an upper portion of the body, and a flat on one side of the body and extending through a portion of the external teeth and located opposite the lip;
each setscrew having a first rotational position when installed in a threaded pocket of the plate wherein the external threads engage the head of an adjacent bone screw situated in an adjacent bone screw bore and the lip engages the first tang of the adjacent bone screw such that backout of the adjacent bone screw is prevented, and a second rotational position when installed in a threaded pocket of the plate wherein the flat of the setscrew is adjacent the bore such that the adjacent bone screw can be inserted into or removed from the bore without restriction.

* * * * *